United States Patent
Brown et al.

(10) Patent No.: US 9,372,151 B2
(45) Date of Patent: Jun. 21, 2016

(54) CROSS ANTENNAS FOR SURFACE-ENHANCED INFRARED ABSORPTION (SEIRA) SPECTROSCOPY OF CHEMICAL MOIETIES

(71) Applicants: Lisa V. Brown, Houston, TX (US); Ke Zhao, Houston, TX (US); Nancy J. Halas, Houston, TX (US); Peter J. Nordlander, Houston, TX (US)

(72) Inventors: Lisa V. Brown, Houston, TX (US); Ke Zhao, Houston, TX (US); Nancy J. Halas, Houston, TX (US); Peter J. Nordlander, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 14/209,310

(22) Filed: Mar. 13, 2014

(65) Prior Publication Data
US 2014/0264026 A1    Sep. 18, 2014

Related U.S. Application Data

(60) Provisional application No. 61/779,377, filed on Mar. 13, 2013.

(51) Int. Cl.
*G01N 21/35* (2014.01)
*G01N 21/552* (2014.01)
*B82Y 40/00* (2011.01)
*B82Y 15/00* (2011.01)

(52) U.S. Cl.
CPC .............. *G01N 21/35* (2013.01); *B82Y 40/00* (2013.01); *G01N 21/553* (2013.01); *B82Y 15/00* (2013.01)

(58) Field of Classification Search
CPC ...... G01N 21/658; G01N 21/35; G01N 21/31
USPC ...................................................... 250/338.1
See application file for complete search history.

(56) References Cited

U.S. PATENT DOCUMENTS

| | | | |
|---|---|---|---|
| 8,492,727 B1* | 7/2013 | Brown et al. | 250/370.07 |
| 2009/0086201 A1* | 4/2009 | Dluhy et al. | 356/301 |
| 2009/0303472 A1* | 12/2009 | Zhao et al. | 356/301 |
| 2011/0212512 A1* | 9/2011 | Wang et al. | 435/288.7 |
| 2011/0249259 A1* | 10/2011 | Van Dorpe et al. | 356/301 |
| 2012/0086021 A1* | 4/2012 | Wang | 257/84 |
| 2012/0154800 A1* | 6/2012 | Natelson et al. | 356/301 |
| 2013/0148194 A1* | 6/2013 | Altug et al. | 359/350 |
| 2013/0235375 A1* | 9/2013 | Katzmann et al. | 356/301 |
| 2014/0224989 A1* | 8/2014 | Long et al. | 250/338.4 |

OTHER PUBLICATIONS

"Quantum Plasmonics: Optical Properties and Tunability of Metallic Nanorods", Jorge Zuloaga, et al., ACSNANO, vol. 4, No. 9, 5269-5276, Aug. 2010 (8 pages).

(Continued)

*Primary Examiner* — Marcus Taningco
(74) *Attorney, Agent, or Firm* — Osha Liang LLP

(57) ABSTRACT

A device for Surface Enhanced Infrared Absorption (SEIRA) that includes at least one pair of metallic antennas deposited on a substrate, wherein the pair of metallic antennas are collinear. The length, width, and height of the metallic antenna determines an infrared absorption of the pair of metallic antennas. The device also includes a gap located between the pair of metallic antennas. A chemical moiety is disposed on at least a portion of the metallic antennas such that the infrared absorption of the chemical moiety is enhanced by the at least one pair of metallic antennas.

11 Claims, 11 Drawing Sheets

(56) References Cited

OTHER PUBLICATIONS

"Resonant Plasmonic and Vibrational Coupling in a Tailored Nanoantenna for Infrared Detection", Frank Neubrech, et al., Physical Review Letters, PRL 101, 157403, Oct. 2008 (4 pages).

"On the Energy Shift between Near-Field and Far-Field Peak Intensities in Localized Plasmon Systems", Jorge Zuloaga, et al., ACS Publications NANO Letters 2011, 11, 1280-1283 (4 pages).

"Terahertz Plasmonic Cross Resonant Antenna", Z. Gao, et al., J. of Electromagn. Waves and Appl., vol. 25, 1730-1739, 2011 (11 pages).

"Cross Resonant Optical Antenna", The American Physical Society, Physical Review Letters PRL 102, 256801, Jun. 2009 (4 pages).

"Broadband plasmonic nanoantenna with an adjustable spectral response", Eren Seydi Unlu, et al., Optics Express, vol. 19, No. 2, 1000-1006, Jan. 2011 (7 pages).

\* cited by examiner

FIG. 4A
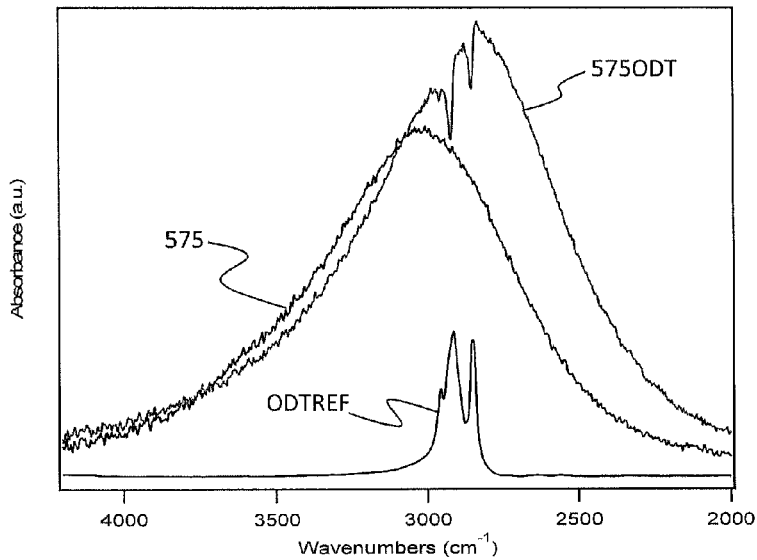
FIG. 4B
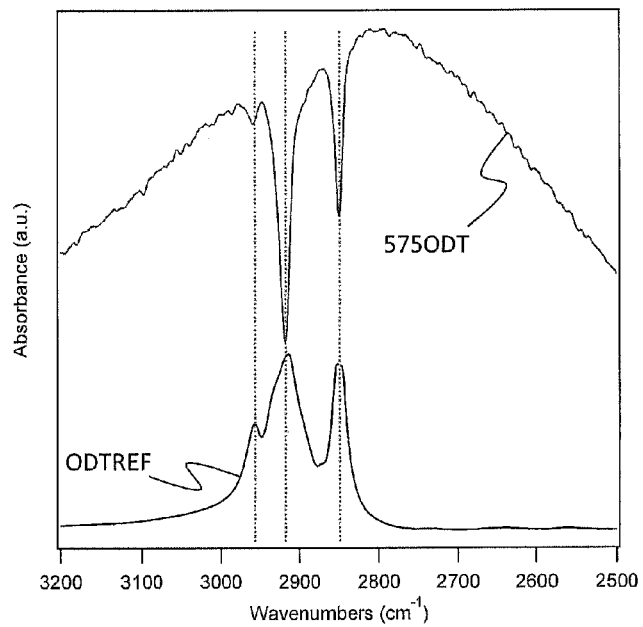
FIGURE 4

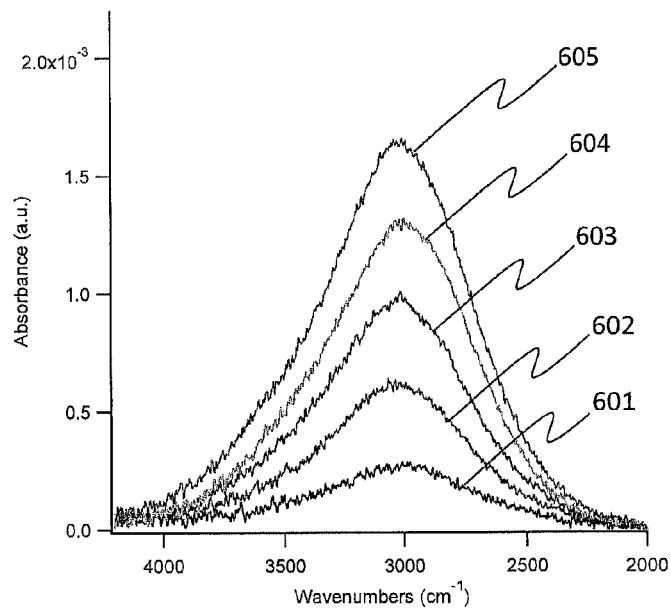
FIG. 6A
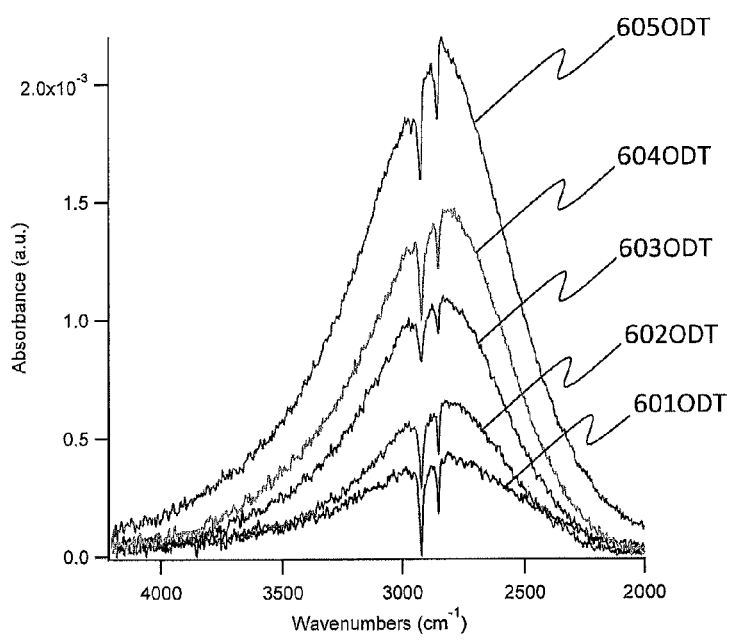
FIG. 6B
FIGURE 6

FIGURE 8 (con't)

FIGURE 10

CROSS ANTENNAS FOR
SURFACE-ENHANCED INFRARED
ABSORPTION (SEIRA) SPECTROSCOPY OF
CHEMICAL MOIETIES

CROSS REFERENCE TO RELATED
APPLICATIONS

Pursuant to 35 U.S.C. §119 (e), this application claims benefit of U.S. Provisional Application No. 61/779,377 filed on Mar. 13, 2013. The disclosure of the U.S. Provisional Application is incorporated herein by reference in its entirety.

STATEMENT REGARDING FEDERALLY
SPONSORED RESEARCH OR DEVELOPMENT

The invention was made with government support under Grant Number FA9550-10-1-0469 awarded by the Air Force Office of Scientific Research. The government has certain rights in the invention The invention was made with government support under Grant Number ECCS-1040478 awarded by the National Science Foundation. The government has certain rights in the invention The invention was made with government support under Grant Number HDTRA1-11-1-0040 awarded by the Defense Threat Reduction Agency. The government has certain rights in the invention The invention was made with government support under Grant Number N00244-09-1-0067 awarded by the DOD, Navy, Office of Naval Research. The government has certain rights in the invention The invention was made with government support under Grant Number W911NF-12-1-0407 awarded by the DOD: Army. The government has certain rights in the invention.

BACKGROUND

Vibrational spectroscopies provide important information concerning the structure, composition, and orientation of molecules. Infrared spectroscopy may be used to determine molecular composition and structure, where the "chemical fingerprints" of functional groups may be obtained by directly exciting dipole-active molecular vibrations with resonant infrared light.

Surface-enhanced strategies have utilized metallic substrates, such as roughened or metal island films or deposited nanoparticles, where molecules are located on or near the structure. The structures may provide an intense, local field enhancement when illuminated, and convey the resulting molecular response effectively to the far field, where it may be detected. The enhancement of vibrational modes is believed to scale as $|E|^2$ of the local field.

The local fields at illuminated metal structures responsible for surface-enhancements are due to excitation of the collective oscillations of the metal electrons of the structure, known as surface plasmons. The size, shape and composition of the metal structure determine the structures resonant frequencies. If a metallic antenna structure has a plasmon resonance at the same frequency as a molecular vibration, the metal and molecule systems may couple, resulting in spectral features with Fano lineshapes characteristic of a coupling between broad and narrow energy states.

For Surface-Enhanced Infrared Absorption (SEIRA), simple antenna structures such as nanorods may provide enhanced IR vibrational signals. However, a high-intensity tunable light source, such as a synchrotron, may be required for adequate signal intensity. For conventional IR sources, large arrays of nanoscale antennas may be required to provide a sufficiently strong signal for detection.

SUMMARY OF INVENTION

In one aspect, embodiments of the invention include a device for Surface Enhanced Infrared Absorption (SEIRA) that includes at least one pair of metallic antennas deposited on a substrate, wherein the pair of metallic antennas are collinear. The length, width, and height of the metallic antenna determines an infrared absorption of the pair of metallic antennas. The device also includes a gap located between the pair of metallic antennas. A chemical moiety is disposed on at least a portion of the metallic antennas such that the infrared absorption of the chemical moiety is enhanced by the at least one pair of metallic antennas.

Other aspects of the invention will be apparent from the following description and the appended claims.

BRIEF DESCRIPTION OF DRAWINGS

FIG. 4A and FIG. 4B show graphs in accordance with one or more embodiments of the invention.

FIG. 6A and FIG. 6B show graphs in accordance with one or more embodiments of the invention.

DETAILED DESCRIPTION

Figure 1A:
FIG. 1A, FIG. 1B, FIG. 1C, and FIG. 1D show schematics of antenna configurations in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention relate to an apparatus for Surface-Enhanced Infrared Absorption (SEIRA) of a chemical moiety. Embodiments of the invention include a cross nanoantenna device that may drastically increase the sensitivity of infrared absorption spectroscopy, a benchmark analytical method for determining the chemical composition of a given material. Previous attempts to improve infrared spectroscopic signals have required the use of large arrays or highly intense synchrotron light sources. Embodiments of the invention may provide a substantial absorption signal with individual antennas using accessible instrumentation and standard light sources.

In this application, the term chemical moiety refers to a chemical structure that may have an absorption in the infrared. The chemical moiety may or may not be covalently bound to the nanoantenna apparatus. Further, the chemical moiety may be assembled piecewise to the nanoantenna apparatus. For example, the chemical moiety may include a capture molecule (disposed on the nanoantenna) and a target molecule. One of ordinary skill in the art will appreciate that chemical reactions, such as covalent or ionic bonding and/or hybridization, may be performed on the surface of the nanoantennas, leading to detectable changed in the SEIRA spectra in accordance with one or more embodiments of the invention. Further, changes in orientation of the chemical moiety may be detectable in accordance with one or more embodiments of the invention.

One or more embodiments of the invention may be used to detect zeptomole quantities of molecules through transmission Fourier transform infrared (FTIR) spectroscopy, in which the chemical vibrations in a given material are detected by infrared light. One or more embodiments of the invention may be used with a commercial FTIR microscope in a conventional laboratory.

Figure 1B:

FIGS. 1A, 1B, 1C, and 1D show schematics of different nanoantenna configurations in accordance with one or more embodiments of the invention. As shown in FIG. 1A, the metallic nanoantennas include two identical rectangular rods/antennas linearly aligned with a gap between each of the antennas. In one or embodiments of the invention, the length, width, height, gap size, and material of the antenna are selected in order to enhance the absorption of a chemical moiety in a desired range of the infrared spectrum. Particularly, the absorption of the nanoantenna is strongly dependent on the aspect ratio of the length to the width of the antenna. In the examples described herein, each rod/antenna has a height of approximately 35 nm, a width of approximately 50 nm, and a length that ranges between 575-1800 nm. In one or more embodiments, as shown in FIG. 1B, at a distance of approximately 75 nm from the end of each antenna at the center of the nanoantenna, the width of the antenna tapers down to a tip with a curvature radius of ~5-10 nm at the gap. In one or more embodiments, the tapered distance may be increased with increasing width of the antenna. In one or more embodiments, for example a nanoantenna that includes one pair of antennas, the distance between opposing tips, i.e., the size of the gap, may be approximately 10 nm. In other embodiments, for example a nanoantenna with two pairs of antennas, the distance between opposing tips may be approximately 35 nm. In one or more embodiments of the invention, the gap between collinear antennas may be made as small as possible using standard lithography techniques, while still achieving the desired infrared absorption.

Figure 1C:
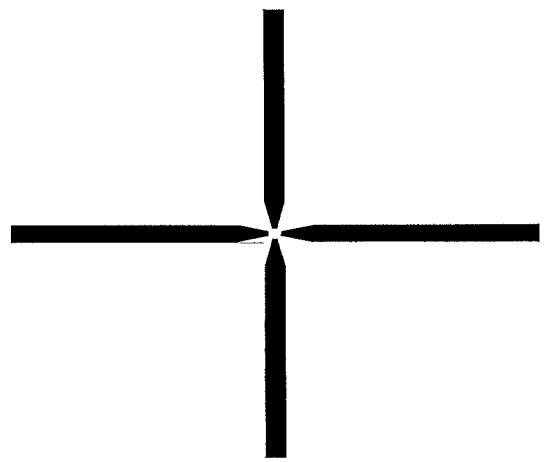

FIG. 1C shows a schematic of a cross configuration of the nanoantennas in accordance with one or more embodiments of the invention. The height and width dimensions of the antennas and the gap are the same as described with reference to FIGS. 1A and 1B. The cross configuration includes two pair or collinear antennas orientated perpendicularly.

Figure 1D:
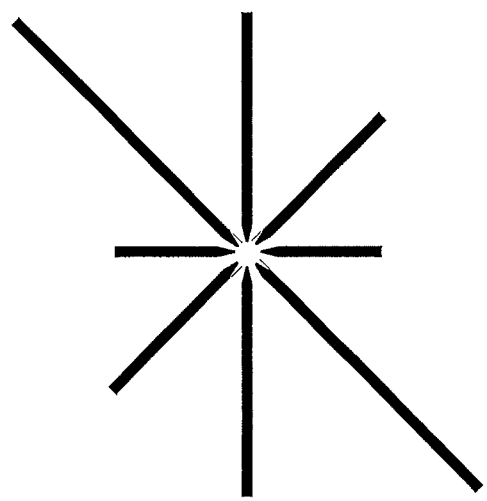

As described below, in accordance with embodiments of the invention, the dimensions and material of the antennas determines the infrared absorption of the nanoantennas. FIG. 1D shows a schematic of a nanoantenna with 4 pairs of antennas, with varying lengths in accordance with one or more embodiments of the invention. The configuration in FIG. 1D allows for absorption in multiple regions of the infrared when using unpolarized light. Further, the configuration shown in FIG. 1D allows for polarization dependent absorption and, hence, polarization dependent enhanced spectroscopy in accordance with one or more embodiments of the invention. FIG. 1D demonstrates that the antenna may have different lengths such that several different chemical vibrations may be enhanced/detected using a single nanoantenna structure.

In the examples demonstrated herein, the nanoantennas are manufactured out of gold; however, one of ordinary skill in the art will appreciate that the embodiments disclosed herein are not limited to gold. For example, gold, silver, aluminum, copper, and nickel may also be used. In the invention, the optical dielectric constant of the material, as well as the physical dimensions, determined the infrared absorption.

In accordance with one or more embodiments of the invention, nanoantennas may be prepared using electron beam lithography according to known techniques. Briefly, polymethyl methacrylate (950 PMMA A2, MicroChem) is applied by spin coating at 3000 rpm, and then the samples are baked on a hot plate at 180° C. for 5 minutes. Espacer 300Z (Showa Denko), a conductive polymer, is applied by spin coating at 3000 rpm on top of the PMMA layer. Electron beam lithography is performed using the Nanometer Pattern Generation System (NPGS) software with an FEI Quanta 600 scanning electron microscope having a beam voltage of 30 kV and a current of 40 pA. The Espacer is then removed by rinsing the sample with deionized water and drying with nitrogen gas. The samples are developed in a 1:3 solution of methyl isobutyl ketone: isopropanol (MicroChem) with subsequent rinsing in isopropanol and drying with nitrogen. A 2-nm adhesion layer of titanium and a 35-nm layer of gold are deposited onto the samples by electron beam evaporation. The remaining PMMA is removed by incubation in N-methyl-2-pyrrolidone (NMP) at 60° C. for 2-3 hours followed by brief submersion in an ultrasound bath at room temperature. Upon removal from the NMP solvent, the samples are again rinsed with isopropanol and dried with nitrogen. To ensure that all residual PMMA is removed, the samples are plasma cleaned with a gas mixture of 25% oxygen balanced with argon for 5 minutes.

In this application, Fourier transform infrared (FTIR) spectra were obtained using a Bruker Vertex 80 v spectrometer and a Hyperion 3000 microscope. The instrument was equipped with a mercury cadmium telluride (MCT) detector, a KBr beam splitter, and a globar light source. The mirror velocity was 20 kHz, and the spectral resolution was 4 cm$^{-1}$. Nearly all optics consisted of uncoated aluminum mirrors for extended ranges. The spectrometer was purged under vacuum, and the microscope was purged with nitrogen gas for at least 3 hours prior to analysis. To purge the microscope stage area, a Plexiglas housing was placed over the front of the microscope. Unpolarized light was used for all measurements unless otherwise noted. After acquiring the data, transmittance spectra were converted to absorbance, and a baseline correction was performed for each spectrum using the OPUS 6.5 software.

In this application, the Finite Element Method (FEM) was used to calculate extinction and field enhancement data in the far-infrared and terahertz regimes. Also, the Finite Difference Time Domain (FDTD) method (Lumerical Solutions software) was used to calculate extinction and near-field enhancement data for cross antennas on an infinitely large ZnSe substrate.

Figure 2:
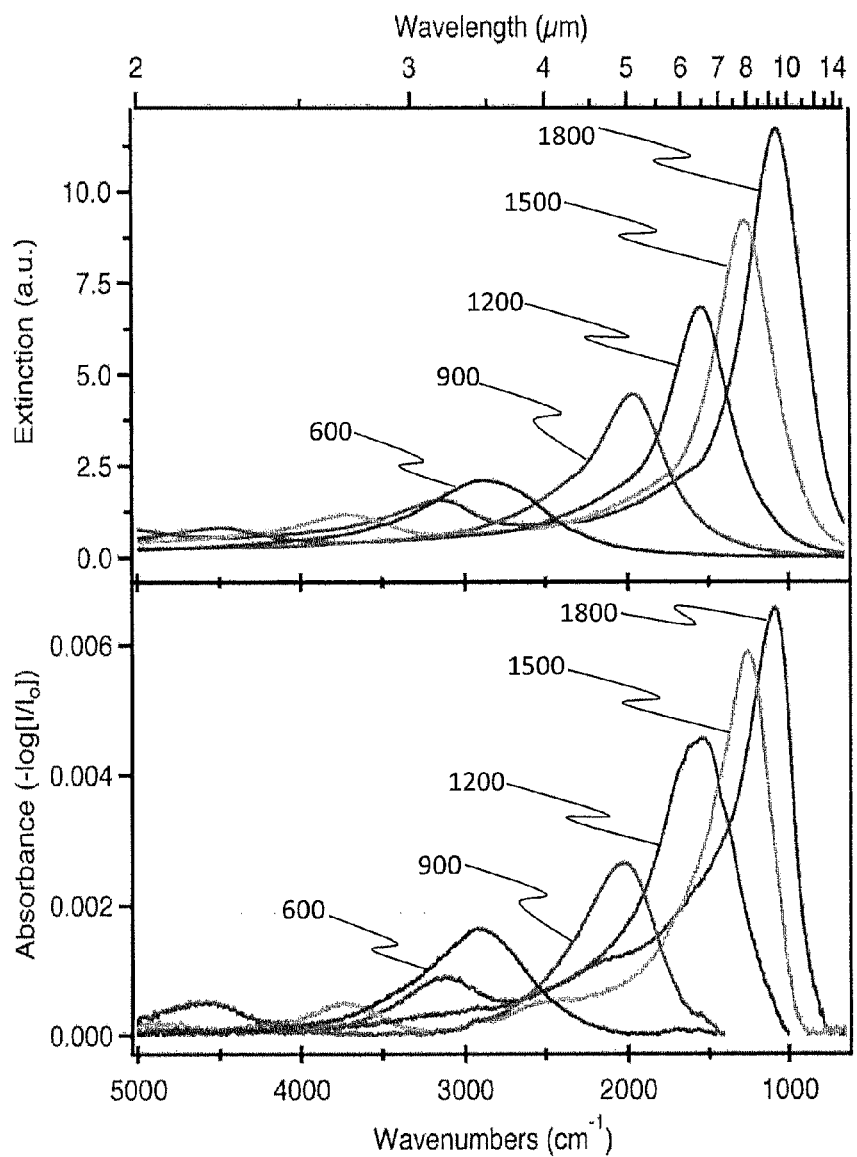
FIG. 2 shows a graph in accordance with one or more embodiments of the invention.

FIG. 2 demonstrates calculated (top) and measured (bottom) Fourier transform infrared (FTIR) absorbance spectra of a cross configuration of the nanoantennas with antenna lengths L=600-1800 nm in accordance with one or more embodiments of the invention. As indicated by the labels, the length of each antenna in the cross configuration is 600 nm, 900 nm, 1200 nm, 1500 nm, and 1800 nm. In accordance with one or more embodiments of the invention, as L is increases, the antenna resonance shifts to lower wavenumbers and increases in intensity. Therefore, by changing the antenna length L, the resonance frequency of the cross antenna can be tuned across the IR region.

Figure 3:
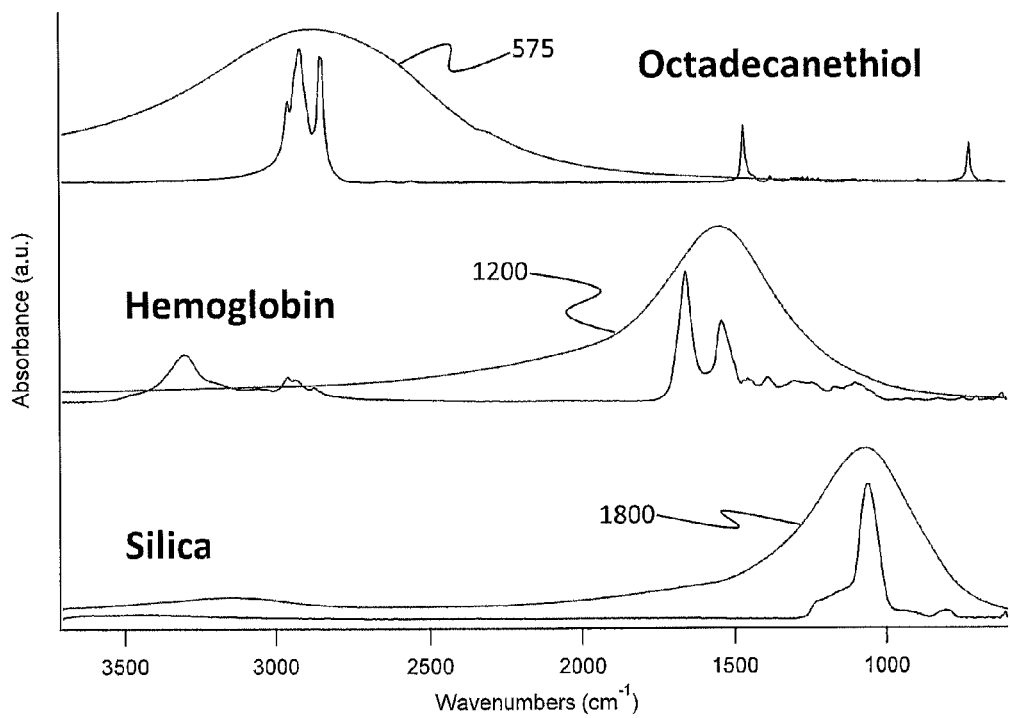
FIG. 3 shows a graph in accordance with one or more embodiments of the invention.

FIG. 3 demonstrates the selection of the antenna length L, with the given width and height, to enhance particular regions of the infrared with respect to different chemical moieties in accordance with one or more embodiments of the invention. As shown at the top of FIG. 3, an antenna length L=575 nm provides a cross nanoantenna infrared resonance that overlaps with the C-H stretches of octadecanethiol (ODT). Similarly, as shown in FIG. 3, antennas with L=1200 and 1800 nm overlap with the amide bands of hemoglobin and the Si—O phonon modes of silica, respectively. The bulk spectra shown in FIG. 3 were obtained from a KBr pellet for ODT and ZnSe substrates for hemoglobin and silica.

FIGS. 4A and 4B demonstrate the enhancement of octadecanethiol (ODT) using a cross configuration of the nanoantennas in accordance with one or more embodiments of the invention. Self-assembled monolayers (SAMs) of ODT were formed and examined using cross antennas with L=575 nm in accordance with one or more embodiments of the invention. The cross configuration nanoantennas were fabricated in a patterns of five cross configuration nanoantennas, where the spacing between the nanoantennas was 10-15 μm to avoid coupling. FIG. 4A shows the FTIR absorbance spectra for the bare nanoantennas 575, the nanoantennas functionalized with ODT 575ODT, and a reference signal of ODT ODTREF in accordance with one or more embodiments of the invention. After functionalizing the sample with ODT, the cross configuration nanoantenna peaks broadened, redshifted, and increased in intensity. In accordance with one or more embodiments of the invention, the redshift may be used to confirm that ODT formed a uniform self-assembled monolayer (SAM) on the nanoantennas.

FIG. 4B demonstrates that the C-H stretch modes are clearly visible as sharp dips within the nanoantenna peaks in the spectral region near 3000 $cm^{-1}$. The modes of the analyte ODT are identified in FIG. 4B by the dashed lines, in which a 5-nanoantenna spectrum 575ODT is compared to a spectrum obtained from an ODT SAM on a blank ZnSe sample ODTREF. In this example, three modes are identified: the symmetric CH2 stretch at 2850 $cm^{-1}$, the asymmetric CH2 stretch at 2919 $cm^{-1}$, and the asymmetric CH3 stretch at 2957 $cm^{-1}$. Detection of the CH3 terminal group indicates the sensitivity of the antennas in accordance with embodiments of the invention, because there is only one CH3 group for each ODT molecule compared to the seventeen methylene groups. The peak positions and relative intensities of the molecular modes shown in FIG. 4B closely match those in the ODT spectrum, as well as a previous study of alkanethiol monolayers on ZnSe.

Additional measurements of similar antenna patterns showed some variations in the intensities of the vibrational modes. Such variations may be caused by subtle differences in the antenna junction geometries or by differences in the specific orientations of the ODT molecules with respect to the polarization of the enhanced near field. As a result of either case, the Fano coupling may be stronger or weaker for different nanoantennas, which may produce some variation in signal intensity. However, observing such differences in the signal may be evidence that only a relatively small number of molecules are contributing to the signal. This small number of molecules may be localized in the center, or junction, of the cross configuration nanoantennas.

Figure 5:
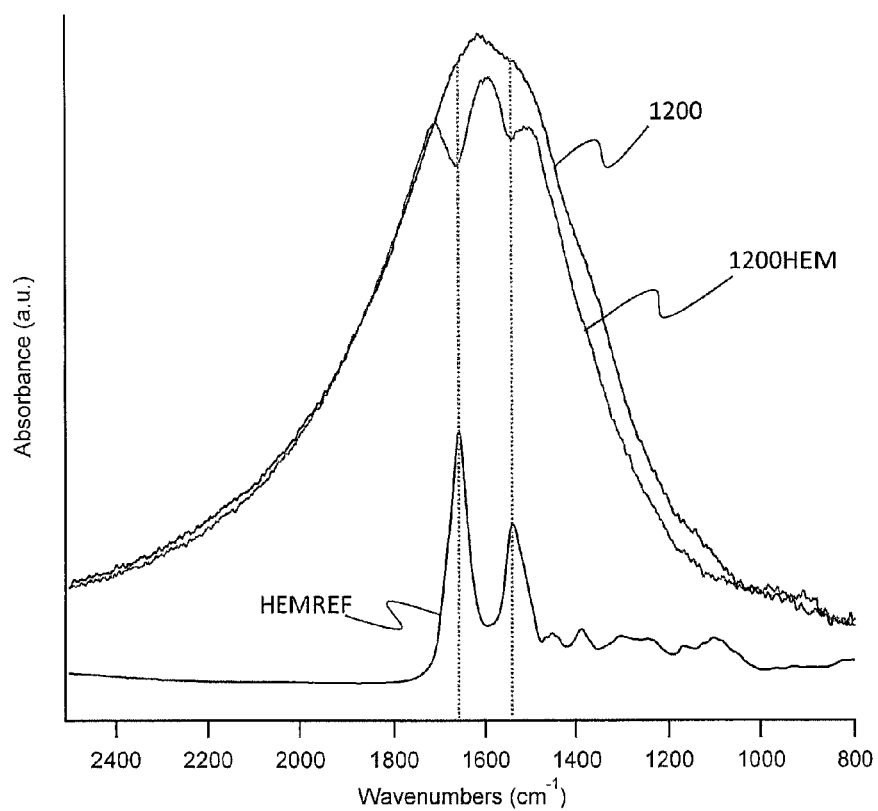
FIG. 5 shows a graph in accordance with one or more embodiments of the invention.

FIG. 5 demonstrates the enhancement of hemoglobin using a cross configuration of four nanoantennas in accordance with one or more embodiments of the invention. In these embodiments, four cross configuration nanoantennas with an antenna length of 1200 nm were used to enhance the amide I and amide II vibrations of hemoglobin. As in FIG. 4, the four cross configuration nanoantennas were spaced 10-15 μm apart to avoid coupling. In these embodiments, after covering the sample with hemoglobin, the nanoantenna resonance peaks 1200HEM did not show a noticeable shift or increase in intensity when compared to the bare nanoantenna peaks 1200. This may indicate that the hemoglobin molecules may have been dispersed across the sample with submonolayer coverage. In each spectrum, the vibrational signals of the amide bonds, as compared to the reference signal HEMREF, appear as dips within the antenna peaks.

The amide I and amide II modes are clearly identifiable (dashed lines) in the antenna spectrum at 1662 and 1540 $cm^{-1}$, respectively. The linewidths of the amide modes are much broader than the C—H modes in FIG. 4 because the amide groups not only vary in orientation, but are also present within several different chemical environments in the hemoglobin molecule.

In contrast to the variations in signal intensity between different antennas observed for ODT, the intensities for hemoglobin are more consistent. This observation suggests that the amide bonds experienced consistent levels of near-field enhancement. Hemoglobin is significantly larger than ODT and may not bind as easily to the interstices of the junction, where any nanoantenna-to-nanoantenna variations in field enhancement are most likely to occur. Also, unlike the uniform arrangement of the C—H bonds in the ODT SAM, the amide bonds within each hemoglobin molecule have different orientations. This may reduce or eliminate variations in signal strength due to orientation dependence of the amide vibrational modes relative to the antenna arms.

FIGS. 6A and 6B demonstrate the dependence of the absorption on the total number of nanoantennas probed in accordance with one or more embodiments of the invention. Specifically, FIG. 6A shows the absorbance of one 601, two 602, three 603, four 604, and five 605 cross configuration nanoantennas. FIG. 6B shows the absorbance of one 601ODT, two 602ODT, three 603ODT, four 604ODT, and five 605ODT cross configuration nanoantennas functionalized with ODT. As shown in FIG. 6A, there is a linear increase in the peak intensity according to the number of antennas. FIG. 6B demonstrates that only one nanoantenna may be used, if desired, in accordance with one or more embodiments of the invention. However, one of ordinary skill in the art will appreciate that the number of nanoantennas may vary, depending on the specific application and/or target chemical moieties.

Figure 7A:
FIG. 7A, FIG. 7B, and FIG. 7C show schematics of antenna configurations in accordance with one or more embodiments of the invention.
Figure 7B:
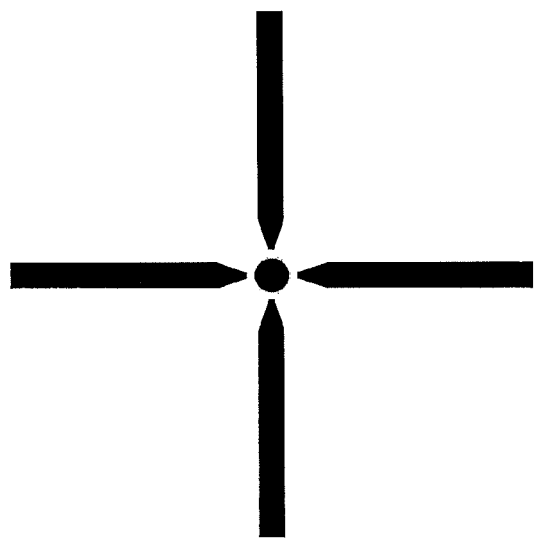
Figure 7C:
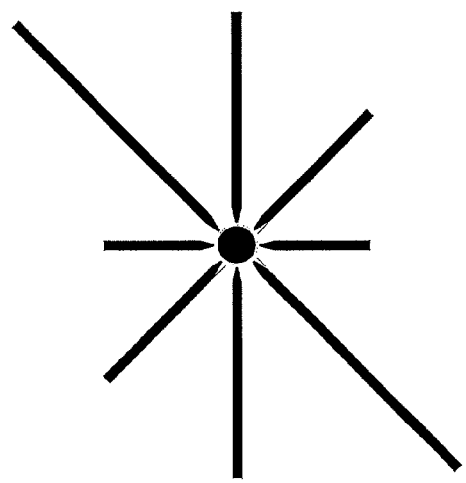

FIGS. 7A, 7B, and 7C show schematics of an alternate configuration of the nanoantenna structure in accordance with one or more embodiments of the invention. The embodiments shown in FIG. 7 are similar to the configurations shown in FIG. 1 with the exception of a disc located within the gap between the antennas. The spacing (gap) between the disc and each of the antennas is approximately 10-15 nm, similar to the gap in the nanoantennas described in FIG. 1. The height of the disc may be selected to be the same as the height of the antenna. The configuration of FIG. 7A demonstrates a nanoantenna with one pair of antennas in accordance with one or more embodiments of the invention. FIG. 7B demonstrates a nanoantenna with two pairs of antennas (cross configuration) in accordance with one or more embodiments of the invention. FIG. 7C shows a nanoantenna with four pairs of antennas with different lengths in accordance with one or more embodiments of the invention. In these embodiments, the additional area of the disc may provide the space for more chemical moieties for enhancement. Further, the inclusion of the disc may provide for the space necessary for including more than 4 pairs of antennas in the nanoantenna device. The diameter of the disc may range from 5 nm to 500 nm. The diameter of the disc may be selected such that the frequency of the constituent antennas will not experience considerable shift in absorbance and also such that the enhancement in the gaps do not decrease in comparison to a nanoantennas device without a disc.

Figure 8A:
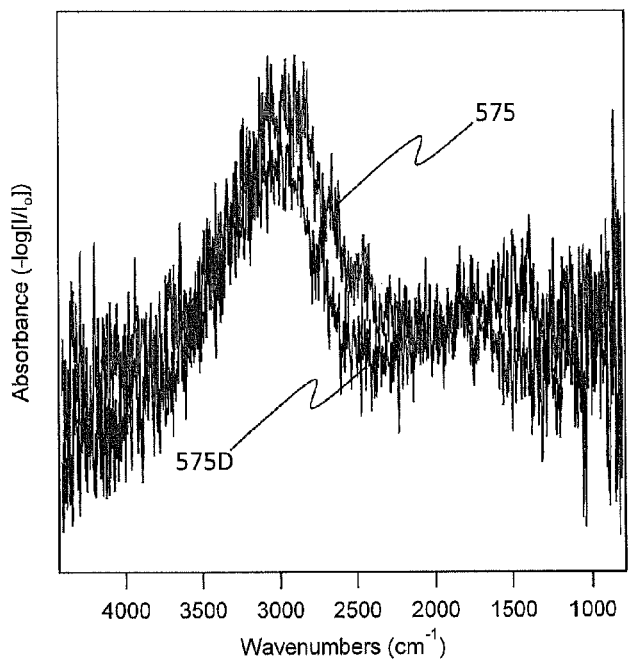
FIG. 8A, FIG. 8B, FIG. 8C, and FIG. 8D show graphs in accordance with one or more embodiments of the invention.
Figure 8B:
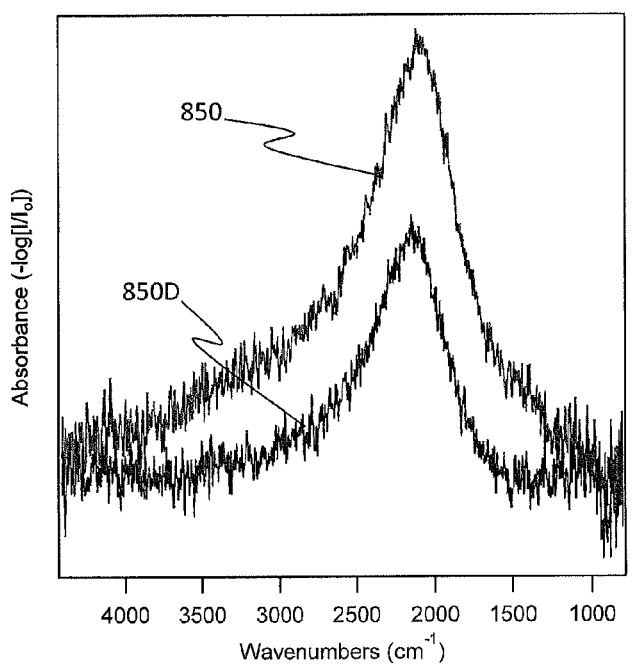
Figure 8C:
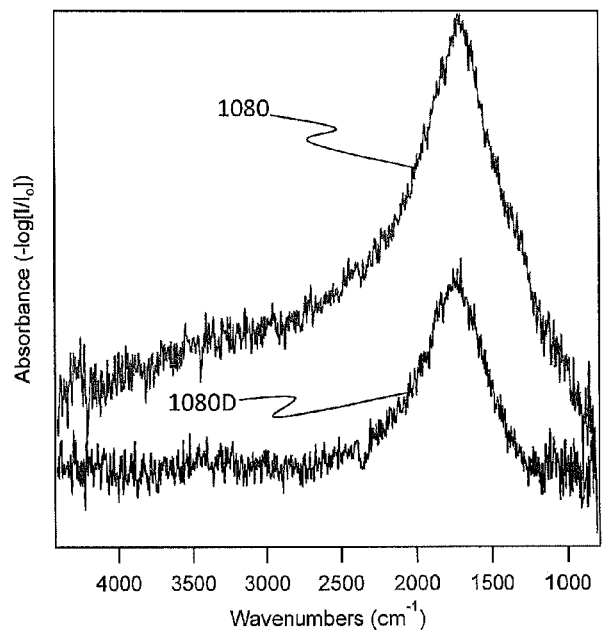
Figure 8D:
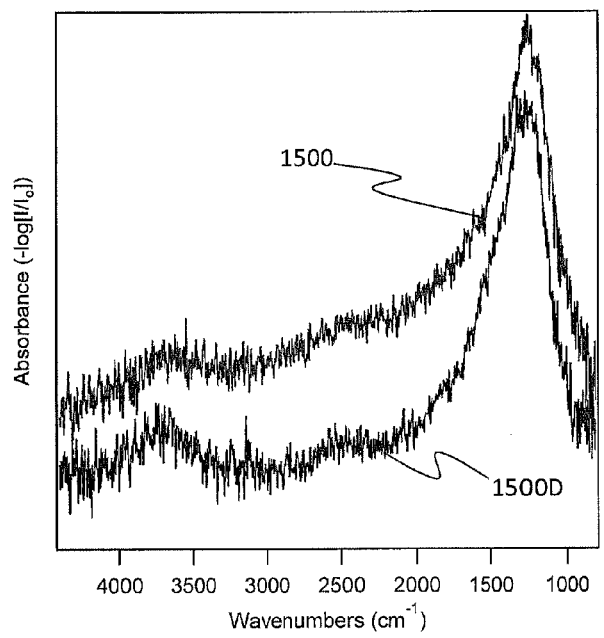

FIGS. 8A, 8B, 8C, and 8D show the absorbance of a single nanoantenna with one pair of antennas with and without the disc in accordance with one or more embodiments of the invention. In FIG. 8A, the single-pair nanoantenna has an antenna length of 575 nm in accordance with one or more embodiments of the invention. The absorbance is shown with 575D and without 575 the disc. FIG. 8B shows a single-pair nanoantenna has an antenna length of 850 nm with 850D and without 850 the disc in accordance with one or more embodiments of the invention. FIG. 8C shows a single-pair nanoantenna has an antenna length of 1080 nm with 1080D and without 1080 the disc in accordance with one or more embodiments of the invention. FIG. 8D shows a single-pair nanoantenna has an antenna length of 1500 nm with 1500D and without 1500 the disc in accordance with one or more embodiments of the invention. FIG. 8 clearly demonstrates that the plasmon resonance location may not change with the addition of the disc.

Figure 9:
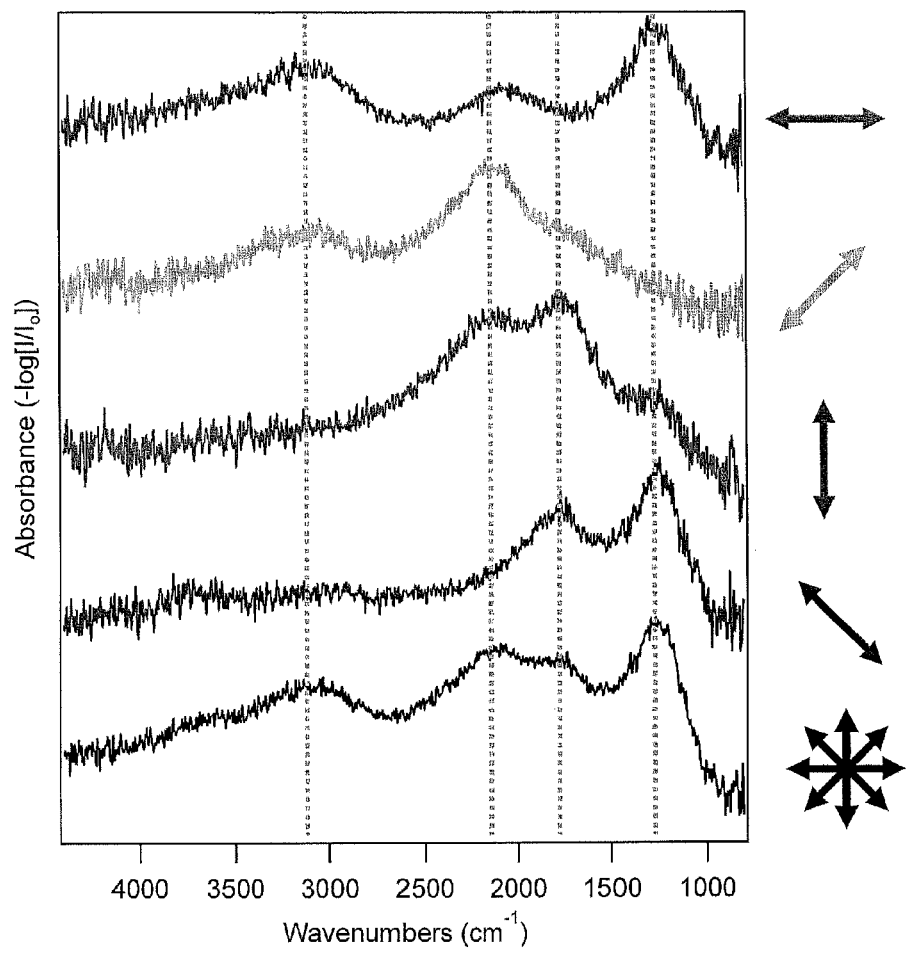
FIG. 9 shows a graph in accordance with one or more embodiments of the invention.

FIG. 9 demonstrates the polarization dependence of the absorbance of a nanoantenna in accordance with one or more embodiments of the invention. The configuration of the nanoantenna demonstrated in FIG. 9 is a four pair nanoantenna with varying lengths of the antennas shown in FIG. 7C. In FIG. 9, the arrow on the right indicates the polarization of the incident infrared light, with the corresponding absorbance shown in the graph. The bottom spectra is the unpolarized incident light. In accordance with one or more embodiments of the invention, the configuration of the nanoantenna, i.e., number of antenna pair, length of antennas, etc., may be selected based on the location of the vibrational states of the target chemical moieties. In one or more embodiments, the polarization may also be used to specifically enhance certain vibrational states, or regions of known vibrational states, of target chemical moieties. Such considerations may be useful in identifying unknown chemical moieties in accordance with one or more embodiments of the invention.

Figure 10A:
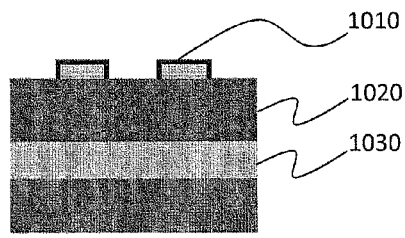
FIG. 10A, FIG. 10B, and FIG. 10C show a schematic and graphs in accordance with one or more embodiments of the invention.
Figure 10B:
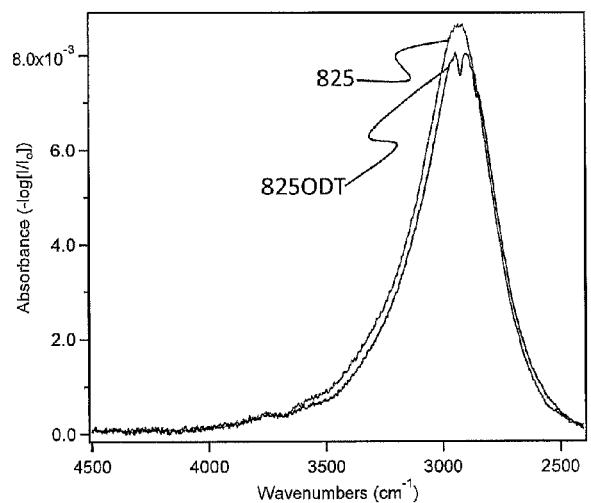
Figure 10C:
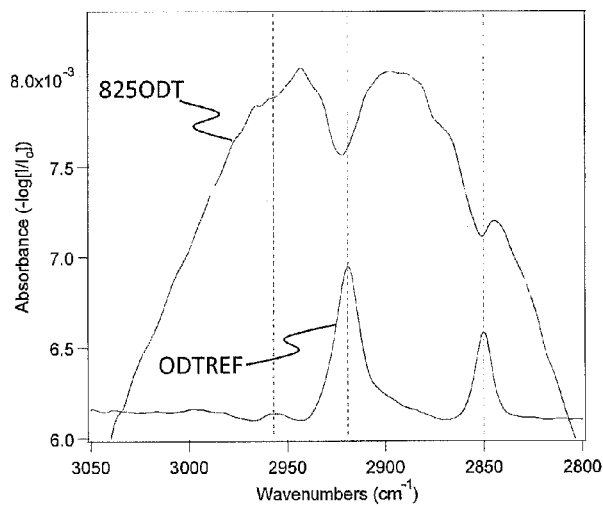

FIG. 10 demonstrates an alternate configuration of the nanoantennas in accordance with one or more embodiments of the invention. As shown in FIG. 10A, the antennas 1010 are deposited onto a dielectric spacer layer 1020 which is deposited onto a metallic film layer 1030 on the substrate 1040. For example, as in FIGS. 10B and 10C, the dielectric spacer layer 1020 may be silica, the metallic film layer 1030 may be gold, and the substrate 1040 may be silicon. In these embodiments, the underlying metallic film may act as a mirror to reflect incident and scattered light, such that the nanoantennas and chemical moieties may be doubly excited and the overall signal intensity may increase. An added advantage of this embodiments may be that certain chemical moieties may selectively adhere to the metallic antennas and not the spacer layer, thus reducing the total quantity of molecules. FIG. 10B shows the absorbance of a cross configuration nanoantenna, consistent with FIG. 10A, with antenna length of 825 nm before 825 and after 825ODT functionalization of ODT in accordance with one or more embodiments of the invention. FIG. 10C shows a different view of the ODT features of the absorbance of the ODT functionalized cross configuration nanoantenna 825ODT, relative to the ODT reference signal ODTREF. The absorbance shown in FIG. 10B was obtained from four cross configured nanoantennas spaced 10-15 μm apart to avoid coupling. A total of ~13.2 attomoles of ODT was deposited; however, it is believed that the majority of the signal is obtained from ~4 attomoles, in the area around the gap.

One or more embodiments of the invention may drastically increase the sensitivity of infrared absorption spectroscopy, a benchmark analytical method for determining the chemical composition of a given material. Embodiments may provide for improved infrared spectroscopic signals without the use of large arrays or highly intense synchrotron light sources. Embodiments of the invention may provide an absorption signal with individual nanoantennas using accessible instrumentation and standard light sources. In addition, embodiments of the invention may be used to detect down to zeptomolar quantities of molecules through transmission Fourier transform infrared (FTIR) spectroscopy. Embodiments of the invention may be used with a commercial FTIR microscope in a conventional laboratory.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An apparatus for Surface Enhanced Infrared Absorption (SEIRA), the apparatus comprising:
    at least one pair of metallic antennas deposited on a substrate, wherein the pair of metallic antennas are collinear;
    wherein the length, width, and height of the at least one pair of metallic antennas determines an infrared absorption of at least one pair of metallic antennas;
    a gap located between the at least one pair of metallic antennas;
    a metallic structure located within the gap;
    a chemical moiety disposed on at least a portion of the at least one pair of metallic antennas,
    wherein the infrared absorption of the chemical moiety is enhanced by the at least one pair of metallic antennas.

2. The apparatus of claim 1, wherein the apparatus comprises three pairs of metallic antennas.

3. The apparatus of claim 1, wherein the apparatus comprises four pairs of metallic antennas.

4. The apparatus of claim 1, wherein the at least one pair of metallic antennas comprises gold.

5. The apparatus of claim 1, wherein a width of each of the metallic antennas in the at least one pair of metallic antennas taper down to a tip with a radius of curvature of approximately 5-10 nm at the gap.

6. The apparatus of claim 1, wherein a height of each metallic antenna is at least 25 nm and the width of each metallic antenna is at least 25 nm.

7. The apparatus of claim 1, wherein the gap between each pair of metallic antennas in the at least one pair of metallic antennas is as small as 10 nm.

8. The apparatus of claim 1, wherein the apparatus comprises a first pair of metallic antennas and a second pair of metallic antennas, wherein the gap between the first pair of metallic antennas and the second pair of metallic antennas is greater than or equal to 25 nm.

9. The apparatus of claim 1, further comprising:
a metallic disc located within the gap, wherein the spacing between the disc and one end of each of the metallic antennas in the at least one pair of metallic antennas is greater than or equal to s 10 nm.

10. The apparatus of claim 1, further comprising:
a metallic layer disposed on the opposite side of the substrate, wherein the substrate is a dielectric material.

11. The apparatus of claim 10, wherein the metallic layer comprises gold.

\* \* \* \* \*